(12) United States Patent
Johnson

(10) Patent No.: US 6,391,555 B1
(45) Date of Patent: May 21, 2002

(54) ASSAY FOR THE DETECTION OF AVIAN LEUKOSIS/SARCOMA VIRUSES (ALSV) IN DNA FROM HUMAN AND ANIMAL BIOLOGICAL SPECIMENS

(76) Inventor: Eric S. Johnson, P.O. Box 51961, New Orleans, LA (US) 70151

( * ) Notice: Subject to any disclaimer, the term of this patent is extended or adjusted under 35 U.S.C. 154(b) by 0 days.

(21) Appl. No.: 09/479,770

(22) Filed: Jan. 7, 2000

Related U.S. Application Data

(60) Provisional application No. 60/115,087, filed on Jan. 7, 1999.

(51) Int. Cl.[7] .......................... C12Q 1/68; C12P 19/34; C07H 21/04
(52) U.S. Cl. .................... 435/6; 435/91.1; 435/91.2; 536/23.1; 536/24.3
(58) Field of Search .................... 435/6, 91.2, 91.1; 536/23.1, 24.3

(56) References Cited

PUBLICATIONS

Johnson et al. Cancer Detection and Prevention, vol. 19, 1995, pp. 394–404.*
Johnson, Cancer Detection and Prevention, vol. 18, pp. 9–30, 1994.*
Kung et al, From: Avian Leukosis, ed: G.F.Deboer, Marinus Nijhoff publishing, pp. 77–99, 1987.*

* cited by examiner

Primary Examiner—W. Gary Jones
Assistant Examiner—Jehanne Souaya
(74) Attorney, Agent, or Firm—Garvey, Smith, Nehrbass & Doody, L.L.C.

(57) ABSTRACT

A method of testing a subject for a propensity to develop, diagnose, or treat ALSV-induced cancer, comprising the steps of obtaining a cell or tissue sample from the subject, processing the sample to isolate DNA from the sample, and examining the DNA isolated from the sample to detect the presence of the ALSV LTR. The sample can be from a cell, a tissue or a tumor. Preferably, the DNA is examined using a PCR-based assay with at least one primer set from the group consisting of: AL1D (SEQ ID NO:1)/AL2B (SEQ ID NO:2), nprA181 (SEQ ID NO:3)/nprA308 (SEQ ID NO:4), nprA271(SEQ ID NO:5)/AL2B (SEQ ID NO:2), RAVO-1 (SEQ ID NO:6)/RAVO-2(SEQ ID NO:7), AL1D(SEQ ID NO:1)/A-Au(SEQ ID NO: 13), S-Au(SEQ ID NO:12)/A-Au(SEQ ID NO:13), and nprA271(SEQ ID NO:5)/A-Au (SEQ ID NO:13), Sn271J(SEQ ID NO:14)/A-AuJ (SEQ ID NO:15).

21 Claims, 14 Drawing Sheets

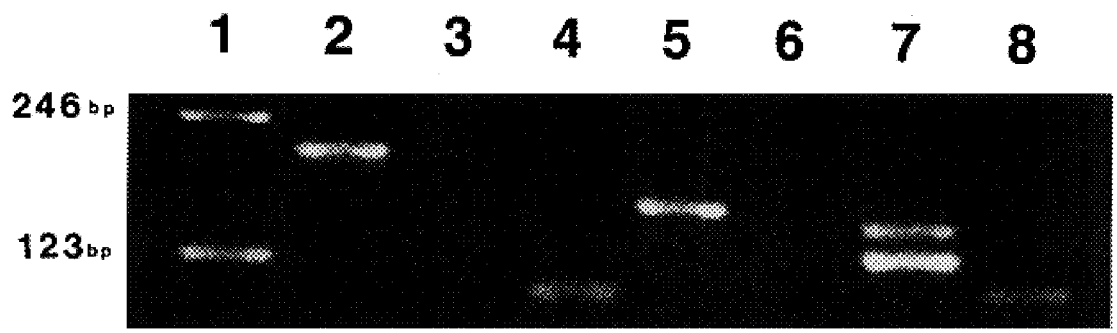
Figure 1. Lane 1, DNA ladder; Lane 2, AL1D/AL2B primers; Lane 3, p19 primers; Lane 4, RAVO primers; Lane 5, Kras primers; Lane 6, No DNA, AL1D/AL2B primers; Lane 7, npr181/npr308 primers; Lane 8, npr271/AL2B primers.

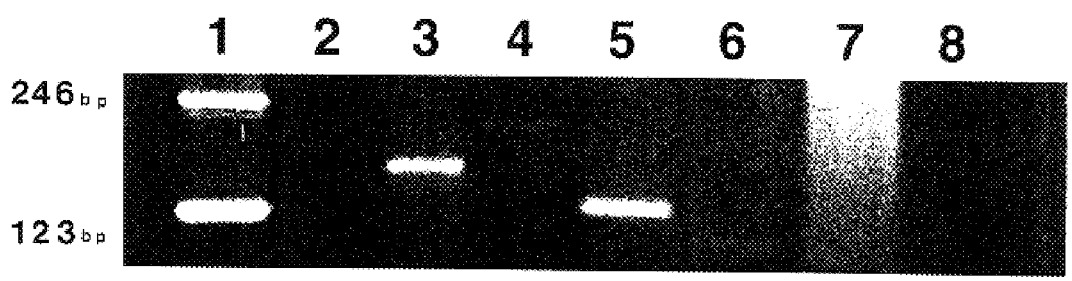
Figure 2. Lane 1, DNA ladder; Lane 2, No DNA, AL1D/AL2B primers; Lane 3, Kras primers; Lane 4, AL1D/AL2B primers; Lane 5, npr181/npr308 primers; Lane 6, npr271/AL2B primers; Lane 7, p19 primers (60 cycles); Lane 8, p19 primers (40 cycles)

Figure 3. Lane 1, DNA ladder; Lane 2, No DNA, AL1D/AL2B primers; Lane 3, Kras primers; Lane 4, AL1D/AL2B primers; Lane 5, npr181/npr308 primers; Lane 6, npr271/AL2B primers; Lane 7, p19 primers (60 cycles); Lane 8, p19 primers (40 cycles)

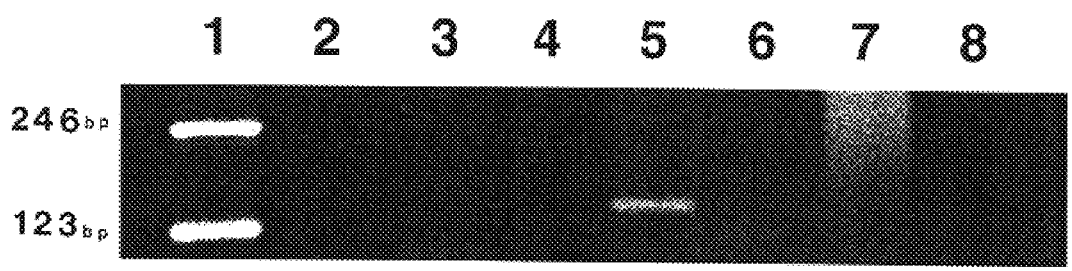
Figure 4. Lane 1, DNA ladder; Lane 2, No DNA, AL1D/AL2B primers; Lane 3, Kras primers; Lane 4, AL1D/AL2B primers; Lane 5, npr181/npr308 primers; Lane 6, npr271/AL2B primers; Lane 7, p19 primers (60 cycles); Lane 8, p19 primers (40 cycles)

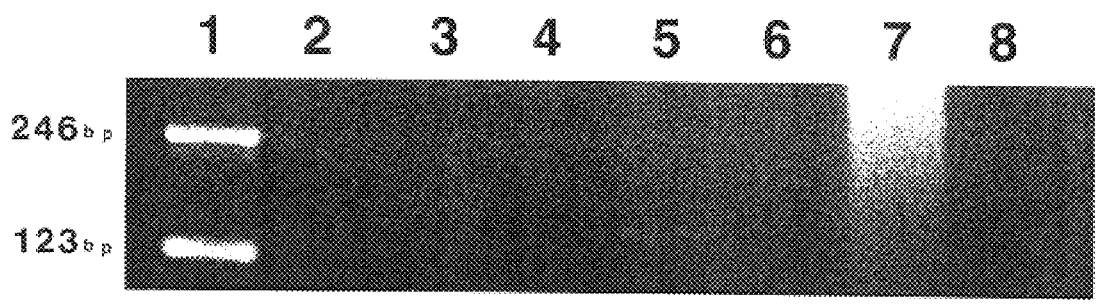
Figure 5. Lane 1, DNA ladder; Lane 2, No DNA, AL1D/AL2B primers; Lane 3, Kras primers; Lane 4, AL1D/AL2B primers; Lane 5, npr181/npr308 primers; Lane 6, npr271/AL2B primers; Lane 7, p19 primers (60 cycles); Lane 8, p19 primers (40 cycles)

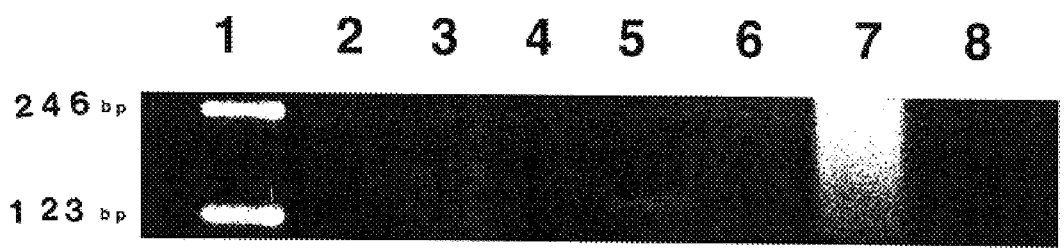
Figure 6. Lane 1, DNA ladder; Lane 2, No DNA, AL1D/AL2B primers; Lane 3, Kras primers; Lane 4, AL1D/AL2B primers; Lane 5, npr181/npr308 primers; Lane 6, npr271/AL2B primers; Lane 7, p19 primers (60 cycles); Lane 8, p19 primers (40 cycles)

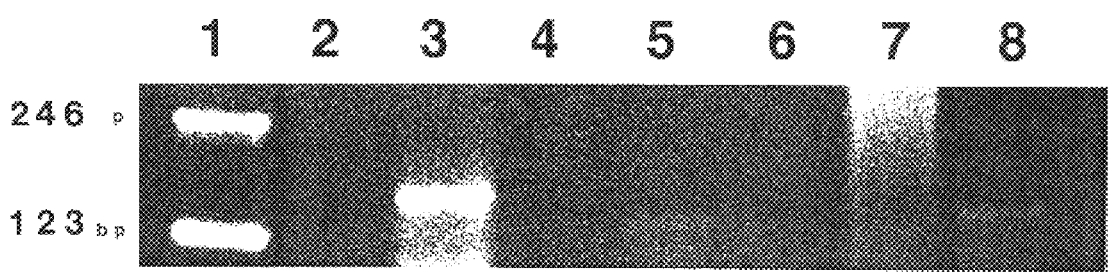
Figure 7. Lane 1, DNA ladder; Lane 2, No DNA, AL1D/AL2B primers; Lane 3, Kras primers; Lane 4, AL1D/AL2B primers; Lane 5, npr181/npr308 primers; Lane 6, npr271/AL2B primers; Lane 7, p19 primers (60 cycles); Lane 8, p19 primers (40 cycles)

```
                      |---------ALID---------|   |---------npr181---------|
R-1366571             NTTGTGCCTTATTAGGAAGGCAACAGACGGGTCTG : ACATGG :
1366571RP                                        CAGACGGGTCTG : ACATGG :
1832107                                          AGGTCTGGACGTGG :
0731793                                          TCTNGACATGGC
1765805B              TTTGTGCNTTATTAGGAAGGCAACAGACGGGTCTG : ACATGG :
9190300R                                         GACGGGTCTA : ACATGG :
LL3B                                             GGTCTG : ACATGGC
PALSV                                            GGTCTG : ACATGG :
L29198                ATCGTGCCTTATTAGGAAGGCAACAGACGGGTCTG : ACATGG :
V01168                ATCGTGCCTTATTAGGAAGGCAACAGACGGGTCTG : ACATGG :
                      1         10        20        30        40
```

| | |
|---|---|
| ---npr181---| |
| R-1366571 | ATTGGACGAACCACTGAATTCCGCATTGCAGAGATATT |
| 136657IRP | ATTGGACGAACCACTGAATTCCGCATTGCAGAGATATT |
| 1832107 | AT:GGACGAACCACTGAATTCCGCATTGCAGAGATATT |
| 0731793 | ATTGGACGAACCACTGAATTCCGCATTGCAGAGATATT |
| 1765805B | ATTGGACGAACCACTGAATTCCGCATTGCAGAGATATT |
| 9190300R | ATTGGACGAACCACTGAATTCCGCATTGCAGAGATATT |
| 9190300 | ATTGGACGAACCACTGAATTCCGCATTGCAGAGATATT |
| LL3B | GAATTCCGCATTGCAGAGATATT |
| pALSV | ATTGGACGAACCACTGAATTCCGCATTGCAGAGATATT |
| L29198 | ATTGGACGAACCACTGAATTCCGCATTGCAGAGATATT |
| V01168 | ATTGGACGAACCACTGAATTCCGCATTGCAGAGATATT |
| | 50       60       70       80 |

| | | |
|---|---|---|
| R-136571 | GTATTTAAGTGCCTAGCTCGATACAATAAACGCCATTTGA | |
| 136571RP | GTATTTAAGTGCCTAGCTCGATACAATAAACGCCATTTGA | |----RAVO-1----|
| 1832107 | GTATTTAAGTGCCTAGCTCGATACAATAAACGCCATTTGA | |----npr271----|
| 0731793 | GTNTTTAANTGCCTAACNCGATACAATANACGCCATTTGA | |
| 1765805B | GTATTTAAGTGCCTAGCTCGATACAATAAACGCCATTTGA | |
| 9190300R | GTATTTAAGTGCCTAGCTCGATACAATAAACGCCATTTGA | |
| 9190300 | GTATTTAAGTGCCTAGCTCGATACAATAAACGCCATTTGA | |
| LL3B | GTATTTAAGTGCCTAGCTCGATACAATAAACGCCATTTGA | |
| pALSV | GTATTTAAGTGCCTAGCTCGATACAATAAACGCCATTTGA | |
| L29198 | GTATTTAAGTGCCTAGCTCGATACAATAAACGCCATTTGA | |
| V01168 | GTATTTAAGTGCCTAGCTCGATACAATAAACGCCATTTGA | |

```
                   |-----RAVO-1-----------|
                   |-----npr271-----------|                           |---------NPR308----------|
R-1366571     CCATTCACCACATTGGTGTGCACCTGGGTTGATGGCCGGA
1366571RP     CCATTCACCACATTG :TGTGCACCTGG g TGATGGCCGGA
1832107          CCATTCACCACATTGGTGTGCACCTGGGTTGATGGCCGGA
0731793          CCATTCNCCNCA :TGGTGTGCNCCTGGGTTGATGGNGGA
1765805B         CCATTCACCACATTGGTGTGCACCTGGGTTGATGGCCGGA
9190300R         CCA
9190300          CCATTCACCACATTGGTGTGCACCTGGGTTGATGGCCGGA
LL3B             CCATTCACCACATTGGTGTGCACCTGGGTTGATGGCCGGA
pALSV            CCATTCACCACATTG :TGTGCACCTGGGTTGATGGCCGGA
L29198           CCATTCACCACATTGGTGTGCACCTGGGTTGATGGCCGGA
V01168           CCATTCACCACATTGGTGTGCACCTGGGTTGATGGCCGGA
                                130        140        150        160
```

|  |  |  | ----RAVO-2---- |
|  |  |  | :-----AL2B----- |
| R-1366571 | CCGTTGATTCCCTG | :ACGACTACGAGCACCTGCATGAAGC |
| 1366571RP | CCGGTGAATCCCNG | :AANAANNNCAACNCCGGCTNAAACN |
| 1832107 | CCGTTGATTCCCTG | :ACGACTACGAGCACCTGCNTGAAGC |
| 0731793 | CCGTTGATTCCNGG | ACGAC |
| 1765805B | CCGTTGATTCCCTG | :ACGACTACGAGCACCTGCATGAAGC |
| LL3B | CCGTTGATTCCCTG | :ACGACTACNAGCACCTGCATGAAGC |
| pALSV | CCGTTGATTCCCTG | :ACGACTACGAGCACCTGCATGAAGC |
| L29198 | CCGTTGATTCCCTG | :ACGACTACGAGCACCTGCATGAAGC |
| V01168 | CCGTTGATTCCCTG | :ACGACTACGAGCACCTGCATGAAGC |
|  | 170            180            190            200 |

```
                                    ----RAVO-2----|
                                    ----AL2B------|
R-1366571   GGAAGGCTTCATACA
1366571RP   GAAAGGNTCCANAAAGGGGG
1832107     GGAAGGCTTCA
0731793
1765805     GGAAGGCTTCA
LL3B        GGAAGGCT
pALSV       GGAAGGCTTC
L29198      AGAAGGCTTCATTTG
V01168      AGAAGGCTTCATT
                      210
```

\* Sample R-1366571 was initially amplified on 2/9/97, while Sample 1366571RP is a repeat PCR amplification of R-1366571 using fresh sample of DNA on 2/15/97.

\*\* Sample 9190300 was sequenced with forward primer nprA181, while 9190300R is the same sample sequenced with the reverse primer nprA308

Figure 8. Sequences amplified by AL1D & AL2B primers. Samples R-1366571, 1832107, 0731793, 1765805, and 9190300 are human tumor samples; LL3B is a sample from ALSV-induced chicken tumor; pALSV is plasmid ALSV DNA; L29198 and V01168 are LTR sequences from GenBank. The sequence for sample 9190300 was amplified by nested primers npr181 and npr308.

United States Patent
US 6,391,555 B1

ASSAY FOR THE DETECTION OF AVIAN LEUKOSIS/SARCOMA VIRUSES (ALSV) IN DNA FROM HUMAN AND ANIMAL BIOLOGICAL SPECIMENS

CROSS-REFERENCE TO RELATED APPLICATIONS

Priority of my U.S. Provisional Patent Application Serial No. 60/115,087, filed Jan. 7, 1999, incorporated herein by reference, is hereby claimed.

My U.S. patent application Ser. No. 08/697,912, filed Aug. 30, 1996, is incorporated herein by reference, as is its full file history.

STATEMENT REGARDING FEDERALLY SPONSORED RESEARCH OR DEVELOPMENT

The inventions disclosed herein were made in part with Government support under identification nos. E-103-94/0, E-104-94/0. The Government may have certain rights in this invention.

REFERENCE TO A "MICROFICHE APPENDIX"

Not applicable

BACKGROUND OF THE INVENTION

1. Field of the Invention

The present invention relates to avian leukosis/sarcoma virus (ALSV)-induced cancer. More particularly, the present invention relates to a method for the detection of the propensity to develop ALSV-induced cancer, and a method to diagnose cancer induced by both exogenous and endogenous ALSV.

2. General Background of the Invention

The following references are incorporated herein by reference:

Johnson, Eric S., Lila Overby, and Richard Philpot, "Detection of Antibodies to Avian Leukosis/Sarcoma Viruses and Reticuloendotheliosis Viruses in Humans by Western Blot Assay", Cancer Detection and Prevention, 19(6):472–486 (1995);

Johnson, Eric S., Lori Nicholson, and David Durack, "Detection of Antibodies to Avian Leukosis/Sarcoma Viruses (ALSV) and Reticuloendotheliosis Viruses (REV) in Humans by ELISA", Cancer Detention and Prevention, 19(5):394–404 (1995);

U.S. Pat. Nos. 5,710,010; 5,716,832; 5,703,055; 5,672,485; 5,591,624; 5,258,299; 5,049,502; 5,028,540; H001065; and all references mentioned herein.

BRIEF SUMMARY OF THE INVENTION

The method of the present invention solves the problems of detecting, diagnosing, and treating ALSV-induced cancer in a simple and straightforward manner. What is provided is a method of 1) testing a subject for a propensity to develop, 2) diagnosing, and 3) treating ALSV-induced cancer, comprising obtaining a sample of cells or tissue from the subject, processing the cell/tissue sample to isolate DNA from the sample, and examining the DNA isolated from the sample to detect the presence of the ALSV LTR. This sample can be, but is not limited to, cells, tissue, or a tumor. The DNA can be examined using a PCR-based assay with the aid of at least one primer set from the group consisting of: AL1D (SEQ ID NO:1)/AL2B (SEQ ID NO:2), nprA181 (SEQ ID NO:3)/ nprA308 (SEQ ID NO:4), nprA271(SEQ ID NO:5)/AL2B (SEQ ID NO:2), RAVO-1(SEQ ID NO:6)/RAVO-2(SEQ ID NO:7), AL1D (SEQ ID NO:1)/A-Au(SEQ ID NO:13), S-Au (SEQ ID NO:12)/A-Au(SEQ ID NO:13), and nprA271(SEQ ID NO:5)/A-Au(SEQ ID NO: 13), Sn271J (SEQ ID NO:14)/ A-AuJ (SEQ ID NO:15).

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein:

FIG. 1 shows the PCR results for subject # 1366571 after 65 cycles of amplification;

FIG. 2 shows the PCR results for sample # 0731793 after 60 cycles of amplification;

FIG. 3 shows the PCR results for sample #1765805 after 60 cycles of amplification;

FIG. 4 shows the PCR results for sample #1832107 after 60 cycles of amplification;

FIG. 5 shows the PCR results for sample #9190300 after 60 cycles of amplification;

FIG. 6 shows the results for DNA from an exogenous ALSV-induced chicken tumor (positive control (LL3B));

FIG. 7 shows the results for DNA from normal chicken cells (negative control (C3D)); and FIG. 8 shows the results obtained for the templates amplified by AL1D (SEQ ID NO:1)(forward) and AL2B (SEQ ID NO:2) (backward) primers.

DETAILED DESCRIPTION OF THE INVENTION

In an as-yet unpublished article entitled "Avian leukosis/ sarcoma Viruses—A new cause of human cancer!" (a copy of which is attached to U.S. Provisional Patent Application Serial No. 60/115,087), the inventor discusses the possibility that human cancer could be caused by avian leukosis/ sarcoma viruses.

The group of avian leukosis/sarcoma viruses (ALSV) include viruses which are among the most potent carcinogenic agents known.[1] In spite of the fact that it has been known for more than 30 years that they can infect and transform human cells in vitro, and can induce tumors in subhuman primates in vivo,[1] for a very long time no further evidence was presented that they pose a potential cancer risk for humans. Recent epidemiological studies now clearly show that subjects with high exposure to these and other oncogenic viruses of cattle and chickens, have increased risk of cancer.[2-13] Furthermore, there is now clear serologic evidence that humans are exposed to ALSV.[14-16] Our studies have been the only ones to have included a cohort of ALSV-exposed workers, and an excess of five cancer types was observed in this group.[2-6,8,9]

The method of the present invention uses a PCR-based assay to detect integrated ALSV provirus in ALSV-exposed cancer patients. By detecting integrated ALSV provirus in the human genome using the method of the present invention, ALSV is shown to be a new cause of human cancer. This information is useful for the diagnosis and treatment of ALSV-induced cancer patients. Furthermore, detection of integrated ALSV provirus in the cells and/or tissues of people who have not yet developed cancer, can help to determine the propensity of that individual developing ALSV-induced cancer in the future. If the ALSV provirus is detected, the likelihood of developing ALSV-induced cancer is significantly greater than if the ALSV provirus is not detected. In addition, detection of integrated ALSV virus in samples from humans who have already developed tumors can lead to the diagnosis of ALSV-induced cancer. This will greatly facilitate treatment, as the treatment can then be made more specific, and hence more effective.

We previously studied cancer mortality risk in a cohort of 28,900 subjects who were members of a local meatcutters' union in Baltimore, Md.[2-9] The cohort included 2,639 subjects who were employed in poultry slaughtering/processing plants, and 10,841 employed in the meat department of supermarkets, with potential exposure to ALSV. An additional 6,081 members of this cohort were employed in companies outside the meat industry such as soft drinks manufacturing and oyster shucking, and had no known occupational exposure to ALSV (control group). We observed statistically significant excess of cancers in five sites including the lung, liver, colon, esophagus, and hemopoietic/lymphatic systems in the group of ALSV-exposed workers, when compared to this control group of nonmeat workers.[2-6,8,9] These results provide, for the first time, confirmation in an analytic epidemiological study, of the association between cancer in humans and poultry.

Because the ALSV-exposed workers had statistically significant excess of cancers of the lung, liver, colon, esophagus, and hemopoietic/lymphatic systems, tissues samples were taken from the tumors that developed in these sites. Tumor samples from a group of subjects who have one of the highest known human exposure levels to ALSV have an increased risk of carrying the integrated virus. We therefore collected paraffin tumor blocks of this specific group of subjects from the hospitals in which death occurred, and have a total of 64 samples in our possession. We present here, the results of the first five samples we have investigated for the presence of the ALSV long terminal repeat (LTR) and gag gene in these tumor samples.

Sources of Paraffin Blocks

Case #1 (No. 1366571) worked in a poultry slaughtering/processing plant for 14 months, and had a death certificate diagnosis of lung cancer as cause of death, at age 50 years. The hospital pathology report on a bone marrow aspirate of which the paraffin tumor block was prepared, indicated metastatic poorly differentiated carcinoma, with lung or gastrointestinal tract as the possible primary site.

Case #2 (No. 9190300) worked in a poultry slaughtering/processing plant for one month, and died at age 51 years with a death certificate diagnosis of malignant melanoma of skin. The hospital pathology report confirmed the death certificate diagnosis.

Case #3 (No. 1832107) worked in a poultry slaughtering/processing plant for three months, and died at age 71 years with a death certificate diagnosis of cancer of the tongue. The hospital pathology report indicated a poorly differentiated squamous cell carcinoma of the tongue.

Case #4 (No. 0731793) worked in a cattle/pig/sheep slaughtering/processing plant which also had an egg-candling facility, for 323 months. Death occurred at age 52 years, with a death certificate diagnosis of lung cancer. The hospital pathology report indicated a moderately differentiated squamous cell carcinoma of the right lung.

Case #5 (No. 1765805) worked in a cattle & pig slaughtering/processing plant for 132 months, and died at age 76 years with a death certificate diagnosis of lung cancer. The hospital pathology reports of both lung biopsy and bronchial washings indicated a moderately differentiated squamous cell carcinoma of the left lung.

DNA was abstracted from a single paraffin block from each subject. To minimize the occurrence of contamination, no plasmid ALSV DNA or DNA from ALSV-positive tumor was handled in the laboratory during the two-week period preceding testing of the first two human DNA samples. For the same reason, no positive control DNA sample (ALSV plasmid DNA or DNA from ALSV-induced chicken tumor) was used concomitantly while these samples were being tested. Primers designed to amplify portions of the ALSV LTR and gag gene were employed.

PCR Results for Subject # 1366571

This was the first sample tested which was positive. The testing was done on Feb. 9, 1997. None of the primers amplified a visible product after the first amplification of 35 cycles. On re-amplification of the PCR products of the first amplification for a further 30 cycles, the following results were obtained as shown in FIG. 1. Lanes 2–5 and 7–8 all contain DNA from the sample obtained from subject #1366571. A presumptively strongly positive band for the ALSV LTR of expected size of 213 bp was obtained with the LTR primers designated AL1D (SEQ ID NO:1)/AL2B (SEQ ID NO:2) (Lane 2). The positivity of this band was confirmed separately by a set of nested primers nprA181 (SEQ ID NO:3)/nprA308 (SEQ ID NO:4) and a set of semi-nested primers nprA271(SEQ ID NO:5)/AL2B (SEQ ID NO:2), which gave bands of the expected sizes of 128 bp and 100 bp, respectively (Lanes 7 & 8). The strong band of around 150 bp above the expected 128 bp in Lane 7 is most likely DNA amplified by excess AL1D (SEQ ID NO:1) primer from the first amplification and nprA308 (SEQ ID NO:4). The other LTR primers RAVO-1(SEQ ID NO:6) & 2 also gave apositive band of the expected 99 bp size, (Lane 4). Similarly, the control Kras primers gave a positive band of size 161 bp as expected (Lane 5), while no band was seen in Lane 6 which contained all PCR reagents, but without any DNA sample (negative control). No band was obtained with the p 191 & 2 primer set, save for a smear (Lane 3). Identical results were obtained for the ALSV primers on repeat of this experiment (on Feb. 15, 1997) using a fresh sample of DNA, and fresh PCR reagents. No further tissue was available for testing, as the initial amount of this sample was very tiny.

PCR Results for Other Human Tumor Samples

The four other human samples were tested concomitantly in the same PCR run, using the same master mix of PCR reagents for each primer set, thus only the DNA was different in these reaction mixtures. As with sample # 13366571, no band was visible after the first amplification for 30 cycles this time, for any of the samples (results not shown). The results for samples #0731793, #1765805, #1832107, and #9190300, after the re-amplification of PCR products of the first amplification for a further 30 cycles are given in FIGS. 2–5. As seen in FIGS. 2–4, samples #0731793, #1765805 and #1832107, gave positive bands with all the LTR primer sets AL1D (SEQ ID NO:1)/AL2B (SEQ ID NO:2), nprA181 (SEQ ID NO:3)/nprA308 (SEQ ID NO:4), and nprA271 (SEQ ID NO:5)/AL2B (SEQ ID NO:2) (Lanes 4,5 & 6), respectively, thus confirming the presence of integrated ALSV LTR. As with sample #1366571, the p191 & 2 primer set did not give a discernible band for these samples also, only a smear was present (Lane 7). However, on re-amplifying first amplification PCR products for only 10 cycles (i.e. a total of 40 cycles) instead of 30 cycles (a total of 60 cycles) the smear disappeared, but no band was evident (Lane 8). The negative control containing all PCR reagents but no DNA gave negative results in each instance, as expected (Lane 2). Kras primers gave a positive band as expected (Lane 3). As seen in FIG. 5, sample #9190300 gave a negative result with the primer set AL1D (SEQ ID NO:1)/AL2B (SEQ ID NO:2) (Lane 4), but a clearly positive result with the nested primer set nprA181 (SEQ ID NO:3)/nprA308 (SEQ ID NO:4) (Lane 5). The semi-nested primer set nprA271(SEQ ID NO:5)/AL2B (SEQ ID NO:2) did not give a visible band of the expected size in this sample (Lane 6). Sometimes the primer sets which include the AL2B (SEQ ID NO:2) primer do not give a visible band even though virus is present. The confirmation of a positive band in such a case is found using the truly nested primers. As with the other human samples, p19 primers gave negative results (Lanes 7 & 8), and the Kras primers gave a positive result for this sample (Lane 3). FIGS. 6 and 7 show the results for DNA from an ALSV-induced chicken tumor, i.e. positive control (LL3B) and from normal chicken cells, i.e. negative control (C3D), respectively. Of the LTR primers, only the nested primer set nprA181 (SEQ ID NO:3)/nprA308 (SEQ ID NO:4) gave a positive result for samples LL3B & C3D (Lane 5, FIGS. 6 & 7). The p19 primer set gave a smear for these samples when the number of second amplification cycles was 30 (Lane 7, FIGS. 6 & 7). However, when the number of cycles was reduced to only 10 (a total of 40, rather than 60 cycles) a positive band was obtained for sample C3D, while sample LL3B was clearly negative (Lane 8, FIGS. 6 & 7).

Tumor DNA from a total of 16 subjects who died of cancer have been tested. In addition, the DNA from peripheral blood lymphocytes from a total of 90 healthy living subjects without known cancer has also been tested. Of the six tumor samples from subjects known to have potential for occupational exposure to ALSV, five were positive on repeated occasions. Of 10 tumor samples from subjects not known to be occupationally exposed to ALSV, only one sample was confirmed positive. However, this subject was known to have worked in a slaughterhouse where cattle, pigs, and sheep were killed, but data were not available as to whether he also worked in a poultry slaughtering house. DNA samples from 45 healthy workers occupationally exposed to ALSV, and 45 controls in the general population without occupational exposure to ALSV were consistently negative on repeated occasions. In other words, ALSV virus could not be detected in a total of 90 apparently healthy subjects, 45 of these subjects had known occupational exposure to ALSV.

Thus, the method of the present invention is useful in detecting the propensity to develop ALSV-induced cancer. Once the ALSV virus integrates permanently into the host genome, the likelihood of tumor development is significantly increased. Thus, routine screening of ALSV-exposed individuals using the method of the present invention would allow early detection of ALSV-integration and thus early detection of ALSV-induced cancer. With repeated testing of a healthy subject, for example but not limited to an annual basis, it is possible to detect integrated virus even before the pending cancer becomes clinically evident. Early cancer detection significantly increases survival.

If this invention method is used to screen the tissue of someone with already clinically evident cancer, determining the presence or absence of ALSV integration is still useful. Knowing the causative agent is helpful in designing a treatment strategy. Detection of the integrated provirus in an individual diagnosed with cancer would indicate the specific cause of the cancer which would then influence subsequent treatment strategy. For example, it would be important to know if the development of a lung cancer in a patient was due to cigarette smoke or to the integration of an ALSV virus. Detection of ALSV virus in that individual would then allow the possibility to develop gene therapies or antibody therapies that target specifically, that integrated virus.

Sequencing Results

Twenty microliters of the PCR product of each human tumor sample and sample LL3B Jan. 6, 1999, obtained after the second amplification with each of the ALSV LTR primers (AL1D (SEQ ID NO:1)/AL2B (SEQ ID NO:2) ;nprA181 (SEQ ID NO:3)/nprA308 (SEQ ID NO:4); nprA271(SEQ ID NO:5)/AL2B (SEQ ID NO:2)), were sent to Commonwealth Biotechnologies Inc., Richmond Va., for sequencing. The results obtained are given in FIG. 8, for the templates amplified by AL1D (SEQ ID NO:1) (forward) and AL2B (SEQ ID NO:2) (backward primers). Using sample #R-1366571 as standard, it was compared with all LTR sequences listed in GenBank. This sample showed closest homology with subgroup A isolates #L29198 (Schmidt-Ruppin) and #V01168 in the GenBank, for which there was perfect homology for at least 210 of the possible 213 bases (99%). There were two discrepancies, a T instead of the C in position 3, and a G instead of the A in position 202, present in these two GenBank isolates. In position 1, the base for sample #R-1366571 was unknown. Sample #1765805 showed the next closest homology to the two GenBank sequences, with disagreement in positions 1,3,43, & 202. Sample #0731793 showed the greatest divergence from the GenBank isolates, involving differences in six positions (36, 43, 97, 134, 174, 176), even though sequence data were not available for 63 base positions for this sample. Strains detected in humans are wild-type, and therefore are expected to be different from the GenBank strains which have been propagated in the laboratory. The positive control chicken tumor induced by ALSV (sample LL3B) showed homology at 181 of the possible 183 positions for which sequence information was available, when compared with the GenBank sequences, with disagreement at only positions 43 & 202. A plasmid ALSV DNA designated pALSV which we had handled in the laboratory on a regular basis was different from the GenBank isolates at also two positions (137 & 202). LL3B and pALSV showed almost 100% homology with human sample #R-1366571, with disagreement in each case at a single different position (43 & 137, respectively). LL3B and pALSV differed from sample #1832107 at four positions in each case, but the differences for LL3B (positions 36, 39, 43, 46) were not all the same as those for pALSV (positions 36, 39, 46, 137). Sample #1832107 also differed from sample R-1366571 in four positions (29,36,39,46). In at least five positions, LL3B differed from human sample #0731793 (36, 97, 134, 174, 176), while pALSV differed from sample #0731793 in at least seven positions (36, 43, 97, 134, 137, 174, 176). Sequence analyses for the bands initially amplified by the nested or semi-nested primers (results not shown) were in perfect agreement with those for the bands amplified by the AL1D (SEQ ID NO:1)/AL2B (SEQ ID NO:2) primer set shown in FIG. 8. Also, in every case above, templates sequenced using the forward primer of a pair showed 100% homology with the corresponding templates sequenced by the backward primer.

Human exposure to viruses of the ALSV group is virtually universal. The highest exposure occurs among subjects involved in the slaughtering and processing of poultry. Cuts and penetrating wounds from bone splinters, knives and cutting machine blades, and frequent occurrence of dermatitis in these workers, offer a ready access for microbial agents to enter the body. Aerosol transmission of microbial agents is also well documented in abattoirs.[17] (Harris, 1962). These workers have intimate contact with internal organs and blood of poultry birds, of which as many as 175,000 can be slaughtered in a day, in a typical large slaughtering plant. Other occupational groups with potential high exposure include veterinarians, laboratory workers and other workers in the meat and food industries. Exposure of the general population is virtually universal, since the viruses are found in commercial eggs and poultry destined for human consumption, and have been shown to survive and remain fully infectious in eggs stored at 8° C. for more than 30 days.[1] The general population can also be exposed when inoculated with vaccines grown on ALSV-contaminated chicken embryo cells, or through the potential use of ALSV as vectors in gene therapy. Thus whether ALSV can infect and cause cancer in humans is of importance.

The results in this study indicate the unequivocal presence of ALSV LTR integrated in the DNA extracted from cancer cells obtained from all five subjects who were members of a Baltimore cohort we had studied and who died of cancer.[3,6;8,9] Three of these workers had definite high exposure to ALSV while working in poultry slaughtering plants, and one with a possible exposure to ALSV while working in a cattle/sheep/pig abattoir/processing plant which also had an egg candling unit. No evidence was available as to whether the fifth subject had occupational exposure to ALSV. It is unlikely that the results obtained could have been due to contamination, since all the PCR reactions with all reagents present except DNA, that were run concomitantly with all the other samples, were always consistently negative. Furthermore, the sequence data showed that the LTR sequences amplified differed across not only the human samples themselves, but also from the only two other sources of exogenous ALSV in our laboratory (LL3B and pALSV). This LTR integration was confirmed using two different sets of primary LTR primers, and two sets of nested or semi-nested primers, and also by oligonucleotide sequencing. DNA extracted separately from a paraffin block of bronchial washings and a paraffin block of lung biopsy tissue from the same subject #1765805 showed identical sequences, hence it is also unlikely that the differences seen between all the samples are due to mutations induced during PCR or contamination. Also, DNA from 45 healthy poultry workers and 45 general population healthy controls which we had available was also negative using the AL1D (SEQ ID NO:1)/AL2B (SEQ ID NO:2) and nprA 181 (SEQ ID NO:3)/nprA308 (SEQ ID NO:4) primers. Taken together, these observations constitute the first evidence that ALSV is involved in human carcinogenesis.

In successful ALSV infection and integration in chickens, the natural host for ALSV, characteristically the LTR is always present, whereas the other genes may be absent if the virus is defective.[18] (Kung & Maihle, 1987). Because of this, our strategy was to first test for presence of ALSV integration in human DNA using LTR primers. The set of p19-1 (SEQ ID NO:8) and p19-2(SEQ ID NO:9) primers failed to amplify any segment of the p19 gag gene in the human and chicken tumors that were positive for ALSV LTR. This could indicate that the integrated virus is defective for at least this segment of the gag gene in these tumors, especially as the p19 gag gene was amplified in the normal chicken tissue sample C3D, probably as part of endogenous ALSV. Both fully replication-competent and defective virus can cause cancer. Because the LTR is always present in tumors, the LTR sequences were used as primers in the present invention. Structural genes such as gag do not have to be present, thus gag sequences may or may not detect the presence of an ALSV provirus in a host genome. The virus can cause cancer in the absence of the gag gene. Thus, the gag gene sequences may not be as useful as the LTR sequences in detecting ALSV provirus using the PCR based assay of the present invention.

It is of interest to know whether this ALSV integration occurs at specific sites in the host cellular genome, such as close to a cellular oncogene or a tumor suppressor gene, or whether other viral genes such as a viral oncogene is involved. If this is the case, additional primers directed to these genes in combination with the LTR primers may also be useful in determining whether or not ALSV has integrated into the host genome. Additionally, if a specific oncogene or tumor suppressor gene is involved, such knowledge will help in the diagnosis and treatment of patients.

This report of the presence of integrated ALSV LTR in the DNA of human subjects dying from cancer should be viewed against the following background: 1) integration is observed in tumor DNA from ALSV-exposed or potentially exposed subjects, but not in DNA from healthy ALSV-exposed human subjects and controls; 2) recent analytic epidemiologic studies have now clearly established that subjects with high occupational exposure to ALSV have excess risk of certain cancers,[3,6,8,9] thus confirming the many previous reports of indirect association between the occurrence of human cancer and putative exposure to ALSV;[1] 3) while the presence of antibodies to ALSV has been clearly demonstrated in the sera of both poultry workers and members of the general population before,[14-16] the present invention demonstrates the presence of integrated ALSV provirus almost exclusively in ALSV-exposed individuals who have died of cancer; 4) experimentally, ALSV has been shown capable of infecting and transforming human cells in vitro,[19,20] 6) ALSV can infect and induce tumors in primates.[1] Taken together, this body of evidence indicates that ALSV is involved in human carcinogenic. Thus, the method of the present invention demonstrates that ALSV detection in tissue samples from humans can be used to determine the propensity to develop, diagnose, and treat ALSV-induced cancer.

Methods

DNA Extraction

Sections of a block of embedded tumor tissue 5 micron thick were cut with a microtome, using a fresh blade for each block. Using a fresh toothpick for each block, 10 to 15 slices of tissue were picked up and deposited in a sterile 1.5 ml Eppendorf tube. The micro tome blade holder and surrounding area and receiving dish were cleaned with ethanol between blocks.

DNA was extracted from paraffin sections using a modified version of the method previously described by Navone et al.[21] Paraffin was removed from the dissected tissue with 1 ml of xylene, vortexes briefly, incubated at 37° C. for 15 minutes, and then centrifuged at 14,000 revolutions per minute (rpm) for 10 minutes. Xylene was decanted, leaving the tissue sediment at the bottom of the tube. Fresh xylene was added to the tissue and the process repeated. After the second xylene decantation, 1 ml of 100 per cent ethanol was added to the tube, the contents briefly vortexes, incubated at room temperature for 5 minutes, and then centrifuged at 14,000 rpm for 10 minutes. Ethanol was decanted, and fresh ethanol added to the precipitate, and the process repeated. After the second ethanol decantation, the precipitate was air-dried at room temperature for 30 minutes, and re-suspended in 200 ul (microliters) of sterile water or TE (Tris/EDTA). The contents were boiled for 5 to 8 minutes to lyse the cells and release the DNA, and then centrifuged at 14,000 rpm for 5 minutes, after which 20 ul of the supernatant was used directly in a PCR reaction without further cleaning or extraction.

Detection of Integrated Virus by Polymerase Chain Reaction (PCR)

A set of oligonucleotide primers designated AL1D (SEQ ID NO: 1) (sense) with sequence of 5'-ATCGTGCCTTATTAGGAA, identified as SEQ ID NO: 1, and AL2B (SEQ ID NO:2) (anti-sense) with sequence of 5'-ATGAAGCCTTCCGCTTCAT, identified as SEQ ID NO:2, were prepared from the long terminal repeat (LTR) segment of ALSV (See Table I for sequence names and numbers). These primers amplify a 213 base pair (bp) product and are derived from a highly conserved region of the LTR. We have previously tested this set of primers on ALSV plasmid DNA and DNA from ALSV-induced chicken tumors and it was always positive in these samples, and negative in DNA samples from healthy human subjects.

TABLE 1

Sequence names and numbers

| Name | SEQ ID NO | Sequence 5'-3' |
|---|---|---|
| AL1D | SEQ ID NO:1 | ATCGTGCCTTATTAGGAA |
| AL2B | SEQ ID NO:2 | ATGAAGCCTTCCGCTTCAT |
| nprA181 | SEQ ID NO:3 | CAGACGGGTCTAACATGGATTGGA |
| nprA308 | SEQ ID NO:4 | ACCCAGGTGCACACCAATGTGG |
| nprA271 | SEQ ID NO:5 | GCCATTTTACCATTCACCAC |
| RAVO-1 | SEQ ID NO:6 | CCATTTTACCATTCACCACATTGGT |
| RAVO-2 | SEQ ID NO:7 | ATGAAGCCTTCTGCTTCATTCAGGT |
| p19-1 | SEQ ID NO:8 | ATCGGGAGAGTTAAAAACCTGGGGA |
| p19-2 | SEQ ID NO:9 | CGGACCTGGGGGAGAGACCCTCCCT |
| Kras-A | SEQ ID NO:10 | ATTTTTATTATAAGGCCTGCTGAAA |
| Kras-B | SEQ ID NO:11 | ATATGCATATTAAAACAAGATTTAC |
| S-Auw | SEQ ID NO:12 | CCACATTGGTGTGCACCTGGGT |
| A-Au | SEQ ID NO:13 | AGCCTTCCGCTTCAT |
| Sn27IJ | SEQ ID NO:14 | GCCATTTTACCTCCCACCAC |
| A-Auj | SEQ ID NO:15 | AGCCATCCGCTTCAT |

We also employed nested primers to confirm any presumptively positive bands obtained with AL1D (SEQ ID NO:1)/AL2B (SEQ ID NO:2) primers. Two separate sets of primers nested within the AL1D/AL2B segment were designed, 1) nprA181 (SEQ ID NO:3) (5'-CAGACGGGTCTAACATGGATTGGA) and nprA308 (SEQ ID NO:4) (5'-ACCCAGGTGCACACCAATGTGG) which amplify a 128 bp segment 2) nprA271(SEQ ID NO:5) (5'-GCCATTTTACCATTCACCAC and AL2B (SEQ ID NO:2) which amplify a 100 bp segment.

We also used two other sets of primers—1) RAVO-1(SEQ ID NO:6) (5'CCATTTTACCATTCACCACATTGGT), SEQ ID NO:6 and RAVO-2(SEQ ID NO:7) (5'ATGAAGCCTTCTGCTTCATTCAGGT), SEQ ID NO:7 which amplify a 99 bp segment of the ALSV LTR, and 2) p19-1(SEQ ID NO:8) (5' ATCGGGAGAGTTAAAAACCTGGGGA), SEQ ID NO:8 and p19-2(SEQ ID NO:9) (5' CGGACCTGGGGGAGAGACCCTCCCT), SEQ ID NO:9 which amplify a 130 bp segment of the p19 ALSV gag gene. Both of these sets of primers consistently gave positive results in PCR assay when used on chicken genome known to contain integrated ALSV. The set of control primers used to monitor the integrity of the human DNA samples was Kras-A(SEQ ID NO: 10) (5'-ATTTTTATTATAAGGCCTGCTGAAA), SEQ ID NO:10 and Kras-B(SEQ ID NO:11) (5'-ATATGCATATTAAAACAAGATTTAC), SEQ ID NO: 11 which amplify a 161 bp segment. An additional primer set that we used included Sn271J (SEQ ID NO: 14 ) and A-AuJ SEQ ID NO:15.

For PCR, two separate reactions were run on a Perkin-Elmer DNA Thermal Cycler Model 480, using PCR reagents from Applied Biosystems—The first 100 uL reaction contained 20 uL of the supernatant containing sample DNA, 16 ul of dNTP mix (final concentration of 200 uM of each dNTP), 10 uL of GeneAmp 10× buffer (100 mM Tris-HCL pH 8.3 at 25° C.; 500 mM KCl; 15 mM $MgCl_2$; 0.01% w/v gelatin) 0.5 uL (2.5 units) of Perkin Elmer AmpliTaq DNA polymerase, 5 uL each (1 uM) of primers AL1D (SEQ ID NO:1) and AL2B (SEQ ID NO:2), and 43.5 uL of sterile water. Reaction conditions consist of denaturing at 94° C. for 1 minute, annealing at 37° C. for 1 minute, and extending at 72° C. for 2 minutes, and amplifying for 35 cycles. In the second 100 uL reaction, 20 uL of PCR product from the first reaction is reamplified using fresh reagents under the same conditions as the first reaction, except that the annealing temperature is increased to 50° C. Taq is increased from 0.5 uL to 1 uL, volume of water is 43 ul and the number of cycles is now 30. Primers used in this second reaction include AL1D (SEQ ID NO: 1) and AL2B (SEQ ID NO:2), control primers, and the nested and seminested primers, at the same concentrations.

Electrophoresis of 8 ul each of PCR product combined with 2 ul bromophenol blue dye, was conducted on 2% Nusieve 3:1 agarose gel (FMC Bioproducts, Richland, Me.) at 70 volts for one and a half hours, using the BRL Model 400 power unit from Life Technologies. Both the gel and electrophoresis bath fluid contained ethidium bromide at a concentration of 50 ug/100 ml.

Sequencing of Amplified PCR Product

Direct sequencing of PCR products was performed by Commonwealth Biotechnologies Inc. Richmond, Va. using the ABI Dye Terminator Cycle Sequencing Ready Reaction Kit, with AmpliTaq DNA Polymerase, FS by Perkin Elmer Corporation, Foster City, Calif. The AmpliTaq DNA Polymerase, FS was developed specifically for fluorescent cycle sequencing with both dye-labeled primers and terminators. Sequence analysis was performed on the ABI 373A DNA Sequencer by Perkin Elmer Corporation.

LTR primers will always detect virus if present as these sequences are needed to integrate into the host genome. Other primers such as those based on the sequences of the gag or env genes will not always do so. Therefore, an LTR-based assay is the most sensitive. The LTR primers used in the assays described herein were designed to be from the most highly conserved areas of the LTR, therefore they are quite sensitive to a variety of different ALSV strains. Other LTR primers may work as well, either singly or in combination with the ones described herein. However, they may be less able to detect as many different strains of ALSV as the ones described in this application either singly or in combination.

We have gone further to develop LTR primers that can be used in this assay to distinguish between exogenous and endogenous ALSV infection or genomic integration in any biological sample, including that of chicken origin. One such primer set is S-Au(SEQ ID NO:12): 5'CCACATTGGTGTGCACCTGGGT, SEQ ID NO: 1 2 and A-Au(SEQ ID NO: 13): 5' AGCCTTCCGCTTCAT, SEQ ID NO:13 (primer concentrations in excess of 1 uM may be necessary in first-round amplification reactions, when the primer A-Au(SEQ ID NO:13) is involved). Results obtained with the set of primers S-Au(SEQ ID NO: 12)/A-Au(SEQ ID NO: 13) or AL1D (SEQ ID NO:1)/A-Au(SEQ ID NO: 13), in combination with results obtained using the various primer sets above such as RAVO 1 &2, etc. can be used to clearly distinguish exogenous from endogenous ALSV infection. This additional feature makes this assay potentially the most sensitive and specific test ever for the detection of ALSV infection in all biological samples of animal origin. The invention applies to any cell or tissue of humans and animals, fresh or embedded.

REFERENCES

1. Johnson, E. S. *Cancer Detect. Prev.* 18, 9–30 (1994).
2. Johnson, E. S., Fischman, H. R., Matanoski, G. M., Diamond, E. *J. Occup. Med.* 28, 23–32 (1986).
3. Johnson, E. S., Fischman, H. R., Matanoski, G. M., Diamond, E. *Br. J. Ind. Med.* 43, 597–604 (1986).
4. Johnson, E. S. *J. Occup. Med* 31, 270–272 (1989).
5. Johnson, E. S. *J. Natl. Cancer Inst.* 83, 1337–1339(1991).
6. Johnson, E. S. *Occup. Environ. Med.* 51, 541–547 (1994).
7. Johnson, E. S., Dalmas, D., Noss, J., Matanoski, G. M. *Am. J. Ind. Med* 27, 389–403 (1995).
8. Johnson, E. S., Shorter, C., Rider, B., Jiles, R. *Int. J Epidemiol.* 26, 1142–1150 (1997).
9. Metayer, C., Johnson, E. S., Rice, J. *Am. J Epidemiol. April* 1998—147, 727–738 (1998).
10. Coggon, D., Pannett, B., Pippard, E. C., Winter, P. D. *Brit. J Ind Med* 46,188–191 (1989).
11. Reif, J. S., Pearce, N. E., Fraser, J. *Scand. J Work Environ. Health* 15, 24–29 (1989).
12. Siemiatycki, J. Ed. *CRC Press.* Boca Raton, Ann Arbor, Boston, London. 1991. pp 225–226.
13. Guberan, E., Usel, M., Raymond, L., Fioretta, G. *Br. J. Ind. Med.* 50, 1008–1016 (1993).
14. Johnson, E. S., Nicholson, L. G., Durack, D. T. *Cancer Det. Prev.* 19, 394–404 (1995).
15. Johnson, E. S., Overby, L., Philpot, R. *Cancer Det. Prev.* 19, 472–486 (1995).
16. Choudat, D., Dambrine, G., Delemotte, B., Coudert, F. *Occup. Environ. Med.* 53, 403–410 (1996).
17. Harris, M. M., Hendricks, S. L., Gorman, G. W., Held, J. R. *Public Health Rep.* 77, 603–604 (1962).
18. Kung, H.-J., Maihie, N. J. Molecular basis of oncogenesis by non-acute avian retroviruses. In: Avian Leukosis. Ed. G. F. De Boer. Martinus Nijhoff Publishing, pp 77–99, 1987.
19. Jensen, F. C., Girardi, A. J., Gilden, R. V., et al. *Proc. Natl. Acad Sci.* (USA) 52, 53–59 (1964).
20. Stenkvist, B., Ponten, J. *Acta Pathol. Microbiol. Scand.* 62, 315–330 (1964)
21. Navone, N. M., Troncoso, P., Pisters, L. L., Goodrow, T. L., Palmer, J. L., Nichols, W. N., von Eschenbach, A. C., Conti, C. J. *J. Natl. Cancer Inst.* 85, 1657–1669 (1993).

ACKNOWLEDGEMENT

I wish to thank, Dr Richard DiAugustine and Mr Charlie Brown for their assistance and support during the initial stage of this work, and hospital pathologists in the State of Maryland who have kindly provided human paraffin tumor blocks. My thanks also Dr Stephen Hughes and Dr. Ron Swanstrom who provided me with ALSV plasmids, and Dr Richard Witter, Dr Aly Fadly and Dr Harriet Robinson who provided me paraffin blocks of chicken tumors.

As used herein, "subject" can mean a human or a non-human.

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

I claim:

1. A method of screening for an increased potential for developing ALSV-induced lung cancer in a subject comprising the steps of:
   (a) obtaining a sample from said subject;
   (b) processing said sample to isolate DNA from said sample;
   (c) examining said DNA isolated from said sample to detect the presence of ALSV nucleic acid sequences,
wherein said presence of said ALSV nucleic acid sequences in said DNA isolated from said subject is indicative of an increased potential for developing ALSV-induced lung cancer.

2. The method of claim 1, wherein said ALSV nucleic acid sequences are ALSV LTR nucleic acid sequences.

3. The method of claim 2, wherein said sample is selected from the group consisting of a tissue, a cell, and a tumor.

4. The method of claim 2, wherein said DNA is examined using a PCR-based assay.

5. The method of claim 4, wherein said PCR-based assay comprises the use of at least one primer set designed to detect said ALSV LTR.

6. The method of claim 5, wherein said at least one primer set is selected from the group consisting of: AL1D (SEQ ID NO:1)/AL2B (SEQ ID NO:2), nprA181 (SEQ ID NO:3)/nprA308 (SEQ ID NO:4), nprA271(SEQ ID NO:5)/AL2B (SEQ ID NO:2), RAVO-1(SEQ ID NO:6)/RAVO-2(SEQ ID NO:7), AL1D (SEQ ID NO:1)/A-Au(SEQ ID NO:13), S-Au (SEQ ID NO:12)/A-Au(SEQ ID NO:13), nprA271(SEQ ID NO:5)/A-Au(SEQ ID NO:13), and Sn271J(SEQ ID NO:14)/A-AuJ (SEQ ID NO:15).

7. A method of diagnosing a cancer patient with ALSV-induced lung cancer, comprising the steps of:
   a. obtaining a sample from said cancer patient;
   b. processing said sample to isolate DNA from said sample;
   c. examining said DNA isolated from said sample to detect the presence of an ALSV LTR;
wherein the presence of said ALSV LTR in said DNA isolated from said cancer patient is indicative of the presence of ALSV-induced lung cancer in said cancer patient.

8. The method of claim 7, wherein said sample is selected from the group consisting of a tissue, a cell, and a tumor.

9. The method of claim 7, wherein said DNA is examined using a PCR-based assay.

10. The method of claim 7, wherein said cancer patient has lung, liver, colon, esophagus, or hemopoietic/lymphatic tumors.

11. The method of claim 9, wherein said PCR-based assay comprises the use of at least one primer set designed to detect said ALSV LTR.

12. The method of claim 11, wherein said at least one primer set is selected from the group consisting of: AL1D (SEQ ID NO:1)/AL2B (SEQ ID NO:2), nprA181 (SEQ ID NO:3)/nprA308 (SEQ ID NO:4), nprA271(SEQ ID NO:5)/AL2B (SEQ ID NO:2), RAVO-1(SEQ ID NO:6)/RAVO-2 (SEQ ID NO:7), AL1D (SEQ ID NO:1)/A-Au(SEQ ID NO:13), S-Au(SEQ ID NO: 12)/A-Au(SEQ ID NO: 13), nprA271 (SEQ ID NO:5)/A-Au(SEQ ID NO:13), and Sn271J(SEQ ID NO:14)/A-AuJ (SEQ ID NO:15).

13. A method of detecting the presence of an integrated ALSV in a host genome, comprising the steps of:
   a. obtaining a sample from the host;
   b. processing said sample to isolate DNA from said sample;
   c. examining said DNA isolated from said sample to detect the presence of a ALSV nucleic acid sequences;
wherein said presence of said ALSV nucleic acid sequences indicates said presence of said integrated ALSV in said host genome, and
wherein said ALSV nucleic acid sequences are ALSV LTR sequences.

14. The method of claim 13, wherein said sample is selected from the group consisting of a tissue, a cell, and a tumor.

15. The method of claim 14, wherein said DNA is examined using a PCR-based assay.

16. The method of claim 15, wherein said PCR-based assay comprises the use of at least one primer set designed to detect ALSV LTR.

17. The method of claim 16, wherein said primer set is selected from the group consisting of: AL1D (SEQ ID NO:1)/AL2B (SEQ ID NO:2), nprA181 (SEQ ID NO:3)/nprA308 (SEQ ID NO:4), nprA271(SEQ ID NO:5/AL2B (SEQ ID NO:2), RAVO-1(SEQ ID NO:6)/RAVO-2(SEQ ID NO:7), AL1D (SEQ ID NO:1)/A-Au(SEQ ID NO:13), S-Au (SEQ ID NO:12)/A-Au(SEQ ID NO:13), nprA271 (SEQ ID NO:5)/A-Au(SEQ ID NO:13), and Sn271J(SEQ ID NO:14)/A-AuJ (SEQ ID NO:15).

18. The method of claim 13, wherein said ALSV LTR is exogenous ALSV LTR.

19. The method of claim 13, wherein said ALSV LTR is endogenous ALSV LTR.

20. An oligonucleotide primer set for use in amplification-based detection of ALSV LTR, wherein said primer set is selected from the group consisting of AL1D (SEQ ID NO:1)/AL2B (SEQ ID NO:2), nprA181 (SEQ ID NO:3)/nprA308 (SEQ ID NO:4), nprA271(SEQ ID NO:5)/AL2B (SEQ ID NO:2), RAVO-1(SEQ ID NO:6)/RAVO-2(SEQ ID NO:7), AL1D (SEQ ID NO:1)/A-Au(SEQ ID NO:13), S-Au (SEQ ID NO:12)/A-Au(SEQ ID NO:13), nprA271 (SEQ ID NO:5)/A-Au(SEQ ID NO:13), and Sn271J(SEQ ID NO:14)/A-AuJ (SEQ ID NO:15).

21. A method for the detection of integrated ALSV in a subject suffering from lung cancer, comprising the steps of:
    (a) isolating DNA from a subject;
    (b) subjecting said DNA to polymerase chain reaction amplification using at least one primer set selected from the group consisting of AL1D (SEQ ID NO:1)/AL2B (SEQ ID NO:2), nprA181 (SEQ ID NO:3)/nprA308 (SEQ ID NO:4), nprA271(SEQ ID NO:5)/AL2B (SEQ ID NO:2), RAVO-1(SEQ ID NO:6)/RAVO-2(SEQ ID NO:7), AL1D (SEQ ID NO:1)/A-Au(SEQ ID NO:13), S-Au(SEQ ID NO:12)/A-Au(SEQ ID NO:13), nprA271(SEQ ID NO:5)/A-Au(SEQ ID NO:13), and Sn271J(SEQ ID NO:14)/A-AuJ(SEQ ID NO:15): and
    (c) detecting said integrated by ALSV by visualizing the product or products of said polymerase chain reaction amplification.

* * * * *

```
SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
          (A) LENGTH: 18 nucleotides
          (B) TYPE: nucleic acid
          (C) STRANDEDNESS: single
          (D) TOPOLOGY: linear (xi) SEQUENCE DESCRIPTION: SEQ ID NO: 1:

ATCGTGCCTT ATTAGGAA                                    18

(2) INFORMATION FOR SEQ ID NO: 2:

(i) SEQUENCE CHARACTERISTICS:
          (A) LENGTH: 19 nucleotides
          (B) TYPE: nucleic acid
```

(C) STRANDEDNESS: single
        (D) TOPOLOGY: linear (xi) SEQUENCE DESCRIPTION: SEQ ID NO: 2:

ATGAAGCCTT CCGCTTCAT                                                19

(2) INFORMATION FOR SEQ ID NO: 3:

(i) SEQUENCE CHARACTERISTICS:
        (A) LENGTH: 24 nucleotides
        (B) TYPE: nucleic acid
        (C) STRANDEDNESS: single
        (D) TOPOLOGY: linear (xi) SEQUENCE DESCRIPTION: SEQ ID NO: 3:

CAGACGGGTC TAACATGGAT TGGA                                          24

(2) INFORMATION FOR SEQ ID NO: 4:

(i) SEQUENCE CHARACTERISTICS:
        (A) LENGTH: 22 nucleotides
        (B) TYPE: nucleic acid
        (C) STRANDEDNESS: single
        (D) TOPOLOGY: linear (xi) SEQUENCE DESCRIPTION: SEQ ID NO: 4:

ACCCAGGTGC ACACCAATGT GG                                            22

(2) INFORMATION FOR SEQ ID NO: 5:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (xi) SEQUENCE DESCRIPTION: SEQ ID NO: 5:

GCCATTTTAC CATTCACCAC                                               20

(2) INFORMATION FOR SEQ ID NO: 6:

(i) SEQUENCE CHARACTERISTICS:
        (A) LENGTH: 25 nucleotides
        (B) TYPE: nucleic acid
        (C) STRANDEDNESS: single
        (D) TOPOLOGY: linear (xi) SEQUENCE DESCRIPTION: SEQ ID NO: 6:

CCATTTTACC ATTCACCACA TTGGT                                         25

(2) INFORMATION FOR SEQ ID NO: 7:

(i) SEQUENCE CHARACTERISTICS:
        (A) LENGTH: 25 nucleotides
        (B) TYPE: nucleic acid
        (C) STRANDEDNESS: single
        (D) TOPOLOGY: linear (xi) SEQUENCE DESCRIPTION: SEQ ID NO: 7:

ATGAAGCCTT CTGCTTCATT CAGGT                                         25

(2) INFORMATION FOR SEQ ID NO: 8:

(i) SEQUENCE CHARACTERISTICS:
        (A) LENGTH: 25 nucleotides
        (B) TYPE: nucleic acid
        (C) STRANDEDNESS: single (D) TOPOLOGY: linear (xi) SEQUENCE DESCRIPTION: SEQ ID NO: 8:

ATCGGGAGAG TTAAAAACCT GGGGA                                              25

(2) INFORMATION FOR SEQ ID NO: 9:

(i) SEQUENCE CHARACTERISTICS:
        (A) LENGTH: 25 nucleotides
        (B) TYPE: nucleic acid
        (C) STRANDEDNESS: single
        (D) TOPOLOGY: linear (xi) SEQUENCE DESCRIPTION: SEQ ID NO: 9:

CGGACCTGGG GGAGAGACCC TCCCT                                              25

(2) INFORMATION FOR SEQ ID NO: 10:

(i) SEQUENCE CHARACTERISTICS:
        (A) LENGTH: 25 nucleotides
        (B) TYPE: nucleic acid
        (C) STRANDEDNESS: single
        (D) TOPOLOGY: linear (xi) SEQUENCE DESCRIPTION: SEQ ID NO: 10:

ATTTTTATTA TAAGGCCTGC TGAAA                                              25

(2) INFORMATION FOR SEQ ID NO: 11:

(i) SEQUENCE CHARACTERISTICS:
        (A) LENGTH: 25 nucleotides
        (B) TYPE: nucleic acid
        (C) STRANDEDNESS: single
        (D) TOPOLOGY: linear (xi) SEQUENCE DESCRIPTION: SEQ ID NO: 11:

ATATGCATAT TAAAACAAGA TTTAC                                              25

(2) INFORMATION FOR SEQ ID NO: 12:

(i) SEQUENCE CHARACTERISTICS:
        (A) LENGTH: 22 nucleotides
        (B) TYPE: nucleic acid
        (C) STRANDEDNESS: single
        (D) TOPOLOGY: linear (xi) SEQUENCE DESCRIPTION: SEQ ID NO: 12:

CCACATTGGT GTGCACCTGG GT                                                 22

(2) INFORMATION FOR SEQ ID NO: 13:

(i) SEQUENCE CHARACTERISTICS:
        (A) LENGTH: 15 nucleotides
        (B) TYPE: nucleic acid
        (C) STRANDEDNESS: single
        (D) TOPOLOGY: linear (xi) SEQUENCE DESCRIPTION: SEQ ID NO: 13:

AGCCTTCCGC TTCAT                                                         15

(2) INFORMATION FOR SEQ ID NO: 14:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (xi) SEQUENCE DESCRIPTION: SEQ ID NO: 14:

GCCATTTTAC CTCCCACCAC                                              20

(2) INFORMATION FOR SEQ ID NO: 15:

(i) SEQUENCE CHARACTERISTICS:
        (A) LENGTH: 15 nucleotides
        (B) TYPE: nucleic acid
        (C) STRANDEDNESS: single
        (D) TOPOLOGY: linear (xi) SEQUENCE DESCRIPTION: SEQ ID NO: 15:

AGCCATCCGC TTCAT                                                   15